(12) United States Patent
Strietzel

(10) Patent No.: US 7,491,361 B2
(45) Date of Patent: Feb. 17, 2009

(54) BURNING-ON ALLOY FOR THE PRODUCTION OF CERAMICALLY VENEERED DENTAL RESTORATIONS

(75) Inventor: Roland Strietzel, Lilienthal (DE)

(73) Assignee: BEGO Bremer Goldschlägerei Wilh. Herbst GmbH & Co. KG, Bremen (DE)

( * ) Notice: Subject to any disclaimer, the term of this patent is extended or adjusted under 35 U.S.C. 154(b) by 122 days.

(21) Appl. No.: 11/355,180

(22) Filed: Feb. 16, 2006

(65) Prior Publication Data

US 2006/0180637 A1    Aug. 17, 2006

(30) Foreign Application Priority Data

Feb. 16, 2005   (EP) ................... 05101162

(51) Int. Cl.
*C22C 19/07*   (2006.01)
*A61C 13/08*   (2006.01)

(52) U.S. Cl. .................. 420/436; 420/435; 420/439; 420/440; 433/207

(58) Field of Classification Search ......... 420/435–440; 433/200.1, 207, 222.1; 148/408, 425
See application file for complete search history.

(56) References Cited

U.S. PATENT DOCUMENTS

| 4,229,215 A | | 10/1980 | Prosen |
| 4,263,045 A | * | 4/1981 | Prosen ........................ 420/440 |
| 4,514,359 A | * | 4/1985 | Andrews ..................... 420/436 |
| 2004/0109785 A1 | | 6/2004 | Lindigkeit |

FOREIGN PATENT DOCUMENTS

| DE | 41 23 606 A1 | 1/1993 |
| DE | 299 09 031 U1 | 8/1999 |
| WO | WO 2004/042098 A | 5/2004 |

* cited by examiner

*Primary Examiner*—J. A. Lorengo
*Assistant Examiner*—Kevin M Johnson
(74) *Attorney, Agent, or Firm*—Roylance, Abrams, Berdo & Goodman, L.L.P.

(57) ABSTRACT

A burning-on alloy for the production of ceramically veneered dental restorations, containing:

| cobalt | 55-65 percent by weight, |
|---|---|
| chromium | 20-30 percent by weight, |
| tungsten and/or molybdenum | where the sum of the content by weight of molybdenum and half the content by weight of tungsten is in the range of 4-12 percent by weight, |
| gallium | 2-4 percent by weight, |
| silicon | 0-2 percent by weight, |
| manganese | 0.05-1.9 percent by weight, |
| nitrogen | 0-0.4 percent by weight, |
| carbon | 0-0.02 percent by weight, |
| vanadium, niobium, tantalum, iron, titanium, zirconium, hafnium | in total 0-5 percent by weight, |
| nickel | 0-0.1 percent by weight, |
| rhenium, gold, silver, copper | in total 0-0.09 percent by weight, |
| other metals, semi-metals and impurities | 0-1 percent by weight, | where the percent by weight data are in each case based on the total weight of the alloy, is described.

19 Claims, No Drawings

BURNING-ON ALLOY FOR THE PRODUCTION OF CERAMICALLY VENEERED DENTAL RESTORATIONS

The invention relates to a burning-on alloy for the production of ceramically veneered dental restorations, for example for the production of crowns, bridges, inlays and other dental prostheses which are to be provided with a ceramic surface.

The alloy according to the invention is a corrosion-resistant alloy based on cobalt/chromium (CoCr-based) which is free from noble metals.

Alloys based on cobalt/chromium are known, for example, from the following publications:

DE 102 31 737 C1, DE 198 45 638 C1, WO 02/36080, WO 00/64403, EP 1 173 136 A1, DE 102 26 221 C1, DE 22 25 577 C3, DE 31 09 053, DE 34 36 118 C1, DE 36 24 377, DE 39 41 820 C2, EP 0 804 934 B1, U.S. Pat. No. 3,366,478, DE 37 44 491 C1, DE 198 15 091 A1, FR 2 750 858 A1, FR 2 750 867 A1, DE 30 38 036 A1, DE 41 23 606 A1, DE 102 52 776 A1, WO 2004/042098 A1, DE 30 01 126 A1, DE 35 10 331 C1 and U.S. Pat. No. 4,263,045:

A number of burning-on alloys based on cobalt/chromium are also commercially obtainable.

In practice, burning-on cobalt/chromium alloys are often veneered with ceramics having a linear thermal expansion coefficient (TEC value) in the range of about $13 \times 10^{-6}/°K$ to $15 \times 10^{-6}/°K$ in the range of 25-500° C. The burning-on alloy according to the invention is also envisaged for veneering with such veneer ceramics.

In the conception of novel burning-on alloys based on cobalt/chromium, the person skilled in the art must take into account a large number of technical properties and attempt to adjust selected properties in a particularly favourable manner, without thereby influencing the other properties in a particularly adverse manner.

In connection with the use of conventional alloys based on cobalt/chromium, persons skilled in the art have hitherto often found it a disadvantage that the correct time of casting cannot be recognized with sufficient certainty; automatic casting time recognition systems are therefore already relatively widely employed as aids.

It has furthermore proved a disadvantage in the use of commercially available CoCr alloys that bridges having a wide span, e.g. 14-membered bridges, produced from the alloy often have only an inadequate fit. Expensive reworking, associated with separating and joining operations in particular, is therefore often necessary.

Furthermore, the manufacturers of burning-on CoCr alloys or veneer ceramics which are compatible with these regularly recommend a process design in which the ceramically veneered structure (dental restoration) is subjected to long-term cooling after sintering, in order to control the TEC of the ceramic in a suitable manner. The TEC of a dental ceramic in fact increases (due to the growth of leucite crystals) if the cooling phase is extended in time. In practice, it is favourable if the TEC of the ceramic is somewhat lower than the TEC of the burning-on alloy to be veneered. In this manner, a required compressive stress can build up in the dental ceramic after the cooling. If the thermal expansion coefficients of the alloy and the dental ceramic are not matched to one another to the optimum, cracks or chips often occur in the ceramic. However, if long-term cooling is carried out in order to match the TEC values of the alloy and ceramic to one another, this is of course a disadvantage, because the dentist must now wait for a longer time before the next working step. For each burning cycle, long-term cooling takes about 10 minutes longer than "normal" cooling.

In view of the problems described above in the use of conventional CoCr alloys, the object on which the present invention was based was to provide a CoCr alloy (i) with which the time of casting is clearly recognizable, (ii) which has a particularly good fit after casting and (iii) with which it is not necessary to carry out long-term cooling after a veneer ceramic has been burned on.

In this context, the other alloy features which are important for a burning-on dental alloy should be within the ranges preferred by the person skilled in the art.

This object is achieved according to the invention by a burning-on alloy for the production of ceramically veneered dental restoration, comprising or containing:

| | |
|---|---|
| cobalt | 55-65 percent by weight, |
| chromium | 20-30 percent by weight, |
| tungsten and/or molybdenum | where the sum of the content by weight of molybdenum and half the content by weight of tungsten is in the range of 4-12 percent by weight, |
| gallium | 2-4 percent by weight, |
| silicon | 0-2 percent by weight, |
| manganese | 0.05-1.9 percent by weight, |
| nitrogen | 0-0.4 percent by weight, |
| carbon | 0-0.02 percent by weight, |
| vanadium, niobium, tantalum, iron, titanium, zirconium, hafnium | in total 0-5 percent by weight, |
| nickel | 0-0.1 percent by weight, |
| platinum group metals, rhenium, gold, silver, copper | in total 0-0.09 percent by weight, |
| other metals, semi-metals and impurities | 0-1 percent by weight, | where the percent by weight data (here and in the following) are in each case based on the total weight of the alloy.

The burning-on alloy according to the invention comprises a content of 55-65 percent by weight of cobalt. It has been found that a higher content of cobalt would lead to an undesirably reduced strength; likewise, a lower content of cobalt, at least with a corresponding increase in the chromium content, would lead to an alloy which becomes brittle in an undesirable manner.

Preferably, the content of cobalt in the alloy according to the invention is 58-62 percent by weight, preferably 59.7-60.7 percent by weight.

The content of chromium in the alloy according to the invention is 20-30 percent by weight. In our own studies, it has been found that a Cr content of less than 20 percent by weight often leads to an unacceptably high corrosiveness of the corresponding alloy and therefore to solubility thereof in the oral cavity. On the other hand, a content of more than 30 percent by weight leads to an alloy which becomes brittle in an unacceptable manner.

Preferably, the content of chromium in the alloy according to the invention is in the range of 23-27 percent by weight, and the range of 24.5-25.5 percent by weight is particularly preferred.

The alloy according to the invention comprises tungsten and/or molybdenum. In this context, the sum of the content by weight of molybdenum and half the content by weight of tungsten is in the range of 4-12 percent by weight, A good compromise between corrosion resistance and mechanical properties, such as hardness, strength and brittleness, is found in this range.

Taking into account the content of chromium in an alloy according to the invention, the following relationship results:

$$[Cr]+3.3(0.5\ [W]+[Mo])>33.2.$$

This value is considerably above the value for the active sum of 30 required according to DIN 13912.

Preferably, in an alloy according to the invention the content of tungsten is in the range of 0-14 percent by weight and/or the content of molybdenum is in the range of 0-10 percent by weight. To establish an advantageous low hardness, the weight ratio of W:Mo is preferably adjusted such that it is greater than 1:2.

The content of molybdenum in an alloy according to the invention is preferably greater than 3.8 percent by weight, since a high corrosion resistance can be achieved in this way.

The content of tungsten in an alloy according to the invention is advantageously greater than 3 percent by weight, and in particular especially if the content of molybdenum is greater than 3.8 percent by weight. In this case, the tungsten has the effect of a desirably low hardness.

Preferred alloys according to the invention have a (quite low) Vickers hardness (HV10) in the range of 260-300, and in this context an HV10 hardness of 275-285 is preferred.

A desirably low hardness and a particularly high corrosion resistance can be achieved in particular with an alloy according to the invention if this comprises 4.8-8.2 percent by weight of tungsten and 3.8-5.8 of molybdenum.

The content of gallium in an alloy according to the invention is in the range of 2-4 percent by weight. In this range of amounts, gallium contributes towards a low hardness, without noticeably reducing the corrosion resistance. Moreover, a favourable adhesive bond to conventional veneer ceramics can be established with an alloy according to the invention due to the gallium content which is present according to the invention.

On the other hand, a content of gallium of more than 4 percent by weight would lead to an unacceptably high brittleness of the finished product (cast piece) and to the formation of oxide layers on the melt during dental casting, which would make determination of the time of casting more difficult. At contents of gallium which are very much higher than those present according to the invention, furthermore, multiphase structures would be formed. At too high a content of gallium, the thermal expansion coefficient of a corresponding alloy would also be too high in many cases, which would involve incompatibility with conventional dental ceramics.

The use of less than 2 percent by weight of gallium would no longer lead to the abovementioned desired effects (influence on hardness, corrosion resistance and adhesive bond).

The content of gallium in an alloy according to the invention is preferably in the range of 2.5-3.3 percent by weight.

The content of silicon in an alloy according to the invention is in the range of 0-2 percent by weight. An increase in the content to a value of greater than 2 percent by weight would lead to a drastic increase in the brittleness and possibly to the formation of undesirable eutectics. Within the range of 0-2 percent by weight, however, silicon act as an oxygen scavenger in a desirable manner. Furthermore, it contributes towards the melting interval of the alloy according to the invention being at a comparatively low temperature and the viscosity of a melt of the alloy according to the invention being comparatively low.

The content of silicon in an alloy according to the invention is preferably in the range of 0.3-2 percent by weight. The use of less than 0.3 percent by weight of silicon would mean that the abovementioned functions of the silicon in an alloy according to the invention can no longer be achieved entirely satisfactorily in the individual case.

The content of manganese in an alloy according to the invention is in the range of 0.05-1.9 percent by weight. In an alloy according to the invention, manganese functions as an oxygen scavenger, agent for forming adhesive oxides and desulfurizing agent. Furthermore, manganese contributes towards the viscosity of a melt of an alloy according to the invention being quite low.

A content of manganese of more than 1.9 percent by weight would lead to an undesirable increase in the TEC value of the corresponding alloy and to less favourable casting properties; in particular, cast pieces cast from a comparison alloy which had a content of manganese of more than 1.9 percent by weight have an undesirable rough surface.

A content of manganese of less than 0.05 percent by weight would mean that the abovementioned functions of the manganese in a corresponding alloy would no longer be achieved entirely satisfactorily in the individual case.

The content of manganese in an alloy according to the invention is preferably 0.05-1 percent by weight.

In all cases, the alloy according to the invention comprises cobalt, chromium and gallium and at least one metal from the group consisting of tungsten and molybdenum. Other constituents are optional.

The content of nitrogen in an alloy according to the invention is in the range of 0-0.4 percent by weight. A low content of nitrogen can thus be tolerated in an alloy according to the invention. Amounts of nitrogen present in an alloy according to the invention lead to a quite high mechanical strength.

The content of carbon in an alloy according to the invention is in the range of 0-0.02 percent by weight. Such low concentrations of carbon can be tolerated in an alloy according to the invention; however, higher contents would often cause trouble; e.g. higher carbon contents during laser welding (e.g. during a repair operation) often lead to embrittlement of the weld seam formed.

The total content of tantalum, iron, titanium, zirconium and hafnium in an alloy according to the invention is in the range of 0-5 percent by weight. Relatively small amounts of the elements mentioned can thus be tolerated in an alloy according to the invention, but a total amount of the compounds mentioned of more than 5 percent by weight would involve an undesirable hardening (increase in hardness) and increase in brittleness.

Preferably, the content of each individual one of the elements vanadium, niobium, tantalum, iron, titanium, zirconium and hafnium in an alloy according to the invention is less than 1 percent by weight.

The content of tantalum in an alloy according to the invention is preferably less than 0.18 percent by weight.

The content of nickel in an alloy according to the invention is in the range of 0-0.1 percent by weight. Higher contents of nickel would increase the risk of contact allergies.

The content of platinum group metals, rhenium, gold, silver and copper in an alloy according to the invention is in the range of 0-0.9 percent by weight.

Other metals, semi-metals and impurities can be present in an alloy according to the invention in the range of 0-1 percent by weight.

In preferred alloys according to the invention, the content by weight of alloying constituents (where present) decreases in the following sequence: cobalt, chromium, tungsten, molybdenum, gallium, silicon, manganese.

A preferred alloy according to the invention does not comprise:

nitrogen and/or carbon and/or vanadium and/or niobium and/or tantalum and/or iron and/or titanium and/or zirconium and/or hafnium and/or nickel and/or metals of the platinum group and/or rhenium and/or gold and/or silver and/or copper.

It is particularly advantageous if none of the elements mentioned last is present in the alloy according to the invention.

Particularly preferred alloys according to the invention contains:

| | | |
|---|---|---|
| cobalt | 60.2 ± 2 | percent by weight, |
| chromium | 25.0 ± 2 | percent by weight, |
| tungsten | 6.2 ± 1 | percent by weight, |
| molybdenum | 4.8 ± 1 | percent by weight, |
| gallium | 2.9 ± 1 | percent by weight, |
| silicon | 0.8 ± 0.3 | percent by weight, |
| manganese | 0.1 ± 0.03 | percent by weight and |
| other constituents | 0-1 | percent by weight. |

A very preferred embodiment example of an alloy according to the invention has the following composition:

| | | |
|---|---|---|
| cobalt | 60.2 | percent by weight, |
| chromium | 25.0 | percent by weight, |
| tungsten | 6.2 | percent by weight, |
| molybdenum | 4.8 | percent by weight, |
| gallium | 2.9 | percent by weight, |
| silicon | 0.8 | percent by weight, |
| manganese | 0.1 | percent by weight. |

The following alloy properties were determined for the particularly preferred alloy according to the invention:

| | |
|---|---|
| density [g/cm$^3$] | 8.5 |
| Vickers hardness [HV 10] | 280 |
| Modulus of elasticity [GPa] | approx. 220 |
| yield strength ($R_p$ 0.2) [MPa] | 540 |
| Tensile strength [MPa] | 680 |
| Elongation at break [A5] [%] | 14 |
| Melting interval [° C.] | 1,360-1,400 |
| Casting temperature [° C.] | approx. 1,500 |
| TEC [$10^{-6}K^{-1}$] 25-500° C. | 14.0 |
| TEC [$10^{-6}K^{-1}$] 25-600° C. | 14.2 |

The alloy according to the invention, in particular in a preferred embodiment, is distinguished in a particularly positive manner by the following properties:
- no long-term cooling is necessary with ceramic veneering, i.e. the processing time is shorter than for the majority of conventional CoCr alloys;
- high fitting accuracy of the structures cast from the alloy (dental restorations);
- comparatively low hardness, i.e. particularly good working/processing properties;
- favourable laser weldability;
- high corrosion resistance;
- favourable recognition of the time of casting (the dentist sees when he must start the casting);
- alloy forms a thinly liquid melt;
- melt of the alloy according to the invention has favourable flow properties (resulting in a high mould filling capacity of the melt);
- alloy can be veneered with all the usual veneer plastics;
- alloy can be veneered with veneer ceramics which have a Thermal Expansion Coefficient in the range of 13-15×$10^{-6}$/°K.

When veneered with ceramic, the alloy according to the invention has the following advantages:
- favourable Thermal Expansion Coefficient;
- favourable chemical adhesion (probably because, in addition to chromium, gallium also acts as an agent which forms adhesive oxides);
- high heat resistance (a structure of the alloy according to the invention does not become distorted during firings);
- all the commercially available ceramics having a Thermal Expansion Coefficient in the range of 13-15×$10^{-6}$/°K can be used;
- "normal" cooling (no long-term cooling) for bridges of all spans (up to 14-membered bridges).

The inventions also relates to a ceramically veneered dental restoration, comprising:
- a dental structure of an alloy according to the invention and
- a dental ceramic burned on to the dental structure having a Thermal Expansion Coefficient in the range of 13-15×$10^{-6}$/°K.

The invention is described in more detail in the following with the aid of an embodiment example:

EMBODIMENT EXAMPLE

1. Production of a 14-Membered Bridge Structure:

A 14-membered upper jaw bridge was modelled from wax; a real patient situation served as the model for this. The minimum wall thickness was in each case 0.3 mm. The anatomical forms were taken into account, so that the majority of the restoration later, after casting, was made of metal.

The wax model produced was embedded in a phosphate-bonded embedding composition.

The resulting muffle was then brought to a temperature of 900° C. (preheating temperature) and held there for 60 min.

Casting was carried out in an induction-heated vacuum-pressure casting machine (Nautilus® T/BEGO, programme 6004) using ingots of an alloy according to the invention of the following composition:

| | | |
|---|---|---|
| cobalt | 60.2 | percent by weight, |
| chromium | 25.0 | percent by weight, |
| tungsten | 6.2 | percent by weight, |
| molybdenum | 4.8 | percent by weight, |
| gallium | 2.9 | percent by weight, |
| silicon | 0.8 | percent by weight, |
| manganese | 0.1 | percent by weight. |

The ingots were heated in the conventional manner. Casting was started manually approx. 4 s after the last solid constituents of the ingots had been immersed in the melt. The time of casting was to be recognized very favourably, since an oxide skin present in the meantime tore open rapidly and clearly.

After cooling of the muffle, the embedding composition was roughly removed mechanically. The bridge structure was then blasted with corundum of grain size 250 μm (Korox® 250/BEGO) under 3 bar. Finally, the surface of the bridge structure was worked with a fine-toothed hard metal mill. Because of the low hardness and the good machinability of the alloy employed, development of the structure was very pleasant for the dentist.

The fit of the structure was strikingly good, compared with experiences from casting other CoCr alloys.

Note: Wobbling to a greater or lesser degree, due to errors in fit, is usually encountered with CoCr alloys. This was very low in two cases of a total of three bridges produced, and in one case was not to be observed. The fit of the two wobbling bridges was eliminated again by separation and joining. For this, in one case laser welding (additional material: Wiroweld/BEGO) and in one case soldering (with Wirobond® solder/BEGO) was used. Both joining techniques can be used without problems and are to be carried out just as in the case of the CoCr alloys obtainable hitherto. The strength of the joined areas was investigated in additional tests in accordance with DIN 13972-2:2002 (laser weldability) and ISO 9333:1990 (soldering). The requirements of the standards were met or exceeded significantly in each case.

2. Veneering of the Bridge Structure with Dental Ceramic by Means of Wash and Ground Coat Firing:

Before the veneering with ceramic, the surface of the bridge structure (from 1. above) was blasted again as described under 1. and evaporated off, in order to condition the surface for a subsequent wash firing.

The wash firing was carried out after application of a thin suspension of a veneer ceramic of the Omega 900 type (Vita). The application here was not opaque.

A ground coat firing was then carried out after application of an opaque layer of powder opaquer of the Omega 900 type (Vita).

For carrying out the wash and ground coat firing, unless stated otherwise here, the procedure followed was in accordance with the processing instructions of the manufacturer of the ceramic (Vita). The temperatures and times stated in the table below were used. A Vakumat 300 (Vita) served as the burning oven.

Slow cooling was omitted, and a normal (i.e. comparatively fast) cooling was carried out. In spite of the normal cooling, surprisingly no cracks or chips appeared, even after leaving to stand for a relatively long time (over 3 days). Due to the normal cooling, the dentist was able to save approx. 10 min in time per firing. The use of the alloy described under 1. therefore renders possible very economical working.

In the process described. oxide firing (before the wash firing) was omitted. However, such a firing can additionally be carried out in order to check the quality of the surface. In the event of an adequate surface quality, no shading should then be detectable, and rather the oxide layer must have a uniform colour. Before the subsequent firings, the oxide layer must be carefully removed again by blasting.

Firings of the type "shoulder coat firing with margin" and "glaze firing with accent fluid" (after the ground coat firing) were omitted in the context of the embodiment example. However, such firings can additionally be carried out.

The following firings were additionally carried out, according to the following table: 1st dentine firing, 2nd dentine firing, correction firing and glaze firing. Ceramic materials of the Omega 900 type (Vita) were again employed here.

The bond strength was determined by in vitro tests (chipping test, quenching test and bending test in accordance with DIN EN ISO 9693:2000). In these, all the requirements were exceeded significantly.

The non-veneered portions (crown edges, but also non-veneered crowns) were very easy to polish. The shine rapidly achieved meets all aesthetic demands and offers great resistance to adhesion of e.g. residues of food and plaque formation.

TABLE

| Firing | Pre-heating temperature [° C.] | Holding time [min] | Heating time [min] | Heating rate [° C./min] | End temperature [° C.] | Holding time [min] | Total vacuum time [min] |
|---|---|---|---|---|---|---|---|
| Wash firing | 600 | 2 | 4 | 75 | 900 | 2 | 4 |
| Ground coat | 600 | 2 | 4 | 75 | 900 | 1 | 4 |
| 1st dentine firing | 600 | 6 | 6 | 50 | 900 | 1 | 6 |
| 2nd dentine firing | 600 | 6 | 6 | 50 | 890 | 1 | 6 |
| Correction firing | 600 | 4 | 6 | 33 | 800 | 1 | 6 |
| Glaze firing | 600 | — | 4 | 75 | 900 | 2 | — |

The invention claimed is:

1. Burning-on alloy for the production of ceramically veneered dental restorations, comprising ingredients according to the following table:

| | |
|---|---|
| cobalt | 55-65 percent by weight, |
| chromium | 20-30 percent by weight, |
| tungsten and molybdenum | where a ratio of tungsten to molybdenum is greater than 1:2 and a sum of the content by weight of molybdenum and half the content by weight of tungsten is in the range of 4-12 percent by weight, |
| gallium | 2-4 percent by weight, |
| silicon | 0-2 percent by weight, |
| manganese | 0.05-1.9 percent by weight, |
| nitrogen | 0-0.4 percent by weight, |
| carbon | 0-0.2 percent by weight, |
| vanadium, niobium, tantalum, iron, titanium, zirconium, hafnium | in total 0-5 percent by weight, |
| nickel | 0-0.1 percent by weight, |
| platinum group metals, rhenium, gold, silver, copper | in total 0-0.09 percent by weight, |
| other metals, semi-metals and impurities | 0-1 percent by weight, | the percent by weight data are in each case based on the total weight of the alloy, whereby the alloy has desired hardness and high corrosion resistance.

2. Alloy according to claim 1, comprising:

| | |
|---|---|
| cobalt | 58-62 percent by weight |
| and chromium | 23-27 percent by weight |
| and tungsten | 0-14 percent by weight |
| and molybdenum | 0-10 percent by weight |
| and gallium | 2.5-3.3 percent by weight |
| and silicon | 0.3-2 percent by weight |
| and manganese | 0.05-1 percent by weight |
| and vanadium, niobium, tantalum, iron, titanium, zirconium, hafnium | in each case less than 1 percent by weight. |

3. Alloy according to claim 1, comprising:

| | |
|---|---|
| cobalt | 59.7-60.7 percent by weight |
| and chromium | 24.5-25.5 percent by weight. |

4. Alloy according to claim 1, comprising:

| | |
|---|---|
| molybdenum | more than 3.8 percent by weight |
| and tungsten | more than 3 percent by weight. |

5. Alloy according to claim 1, comprising

| | |
|---|---|
| tungsten | 4.2-8.2 percent by weight |
| and molybdenum | 3.8-5.8 percent by weight. |

6. Alloy according to claim 1, wherein the content by weight of alloying constituents, where these are present, decreases in the following sequence:
cobalt, chromium, tungsten, molybdenum, gallium, silicon, manganese.

7. Alloy according to claim 1, which does not comprise:
nitrogen, carbon, vanadium, niobium, tantalum, iron, titanium, zirconium, hafnium, nickel, metals of the platinum group, rhenium, gold, silver or copper.

8. Alloy according to claim 1 which comprises:

| | |
|---|---|
| cobalt | 60.2 ± 2 percent by weight, |
| chromium | 25.0 ± 2 percent by weight, |
| tungsten | 6.2 ± 1 percent by weight, |
| molybdenum | 4.8 ± 1 percent by weight, |
| gallium | 2.9 ± 1 percent by weight, |
| silicon | 0.8 ± 0.3 percent by weight, |
| manganese | 0.1 ± 0.03 percent by weight and |
| other constituents | 0-1 percent by weight. |

9. Ceramically veneered dental restoration, comprising:
a dental structure of an alloy according to claim 1 and
a dental ceramic burned on to the dental structure having a Thermal Expansion Coefficient in the range of $13 \times 10^{-6}/°K$ to $15 \times 10^{-6}/°K$.

10. Alloy according to claim 1, comprising:

| | |
|---|---|
| cobalt | 58-62 percent by weight |
| or chromium | 23-27 percent by weight |
| or tungsten | 0-14 percent by weight |
| or molybdenum | 0-10 percent by weight |
| or gallium | 2.5-3.3 percent by weight |
| or silicon | 0.3-2 percent by weight |
| or manganese | 0.05-1 percent by weight |
| or vanadium, niobium, tantalum, iron, titanium, zirconium, hafnium | in each case less than 1 percent by weight. |

11. Alloy according to claim 1, comprising:

| | |
|---|---|
| cobalt | 59.7-60.7 percent by weight |
| or chromium | 24.5-25.5 percent by weight. |

12. Alloy according to claim 1, comprising:

| | |
|---|---|
| molybdenum | more than 3.8 percent by weight |
| or tungsten | more than 3 percent by weight. |

13. Alloy according to claim 1, which does not comprise at least one constituent selected from either nitrogen, carbon, vanadium, niobium, tantalum, iron, titanium, zirconium, hafnium, nickel, metals of the platinum group, rhenium, gold, silver or copper.

14. Alloy according to claim 1, wherein a Vickers hardness of the alloy is in the range of 260 to 300.

15. Alloy according to claim 14, wherein the Vickers hardness of the alloy is in the range of 275-285.

16. Burning-on alloy for the production of ceramically veneered dental restorations, comprising ingredients according to the following table:

| | |
|---|---|
| cobalt | 55-65 percent by weight, |
| chromium | 20-30 percent by weight, |
| tungsten | 4.2-8.2 percent by weight, |
| molybdenum | 3.8-8.5 percent by weight, |
| gallium | 2-4 percent by weight, |
| silicon | 0-2 percent by weight, |
| manganese | 0.05-1.9 percent by weight, |
| nitrogen | 0-0.4 percent by weight, |
| carbon | 0-0.2 percent by weight, |
| vanadium, niobium, tantalum, iron, titanium, zirconium, hafnium | in total 0-5 percent by weight, |
| nickel | 0-0.1 percent by weight, |
| platinum group metals, rhenium, gold, silver, copper | in total 0-0.09 percent by weight, |
| other metals, semi-metals and impurities | 0-1 percent by weight, | the percent by weight data are in each case based on the total weight of the alloy.

17. Burning-on alloy for the production of ceramically veneered dental restorations, comprising ingredients according to the following table:

| | |
|---|---|
| cobalt | 55-65 percent by weight, |
| chromium | 20-30 percent by weight, |
| tungsten | 4.2-8.2 percent by weight, |
| molybdenum | 3.8-8.5 percent by weight, |
| gallium | 2-4 percent by weight, |
| silicon | 0-2 percent by weight, |
| manganese | 0.05-1.9 percent by weight, |
| nitrogen | 0-0.4 percent by weight, |
| carbon | 0-0.2 percent by weight, |
| vanadium, tantalum, iron, titanium, zirconium, hafnium | in total 0-5 percent by weight, |
| nickel | 0-0.1 percent by weight, |

| -continued | |
|---|---|
| platinum group metals, rhenium, gold, silver, copper | in total 0-0.09 percent by weight, |
| other metals, semi-metals and impurities | 0-1 percent by weight, | the percent by weight data are in each case based on the total weight of the alloy, where the alloy does not include niobium.

18. Burning-on alloy for the production of ceramically veneered dental restorations, comprising ingredients according to the following table:

| | |
|---|---|
| cobalt | 55-65 percent by weight, |
| chromium | 20-30 percent by weight, |
| tungsten | 4.2-8.2 percent by weight, |
| molybdenum | 3.8-8.5 percent by weight, |
| gallium | 2-4 percent by weight, |
| silicon | 0-2 percent by weight, |
| manganese | 0.05-1.9 percent by weight, |
| nitrogen | 0-0.4 percent by weight, |
| carbon | 0-0.2 percent by weight, |
| vanadium, tantalum, niobium, iron, titanium, zirconium, hafnium | in total 0-5 percent by weight, |
| nickel | 0-0.1 percent by weight, |
| platinum group metals, rhenium, gold, silver | in total 0-0.09 percent by weight, |
| other metals, semi-metals and impurities | 0-1 percent by weight, | the percent by weight data are in each case based on the total weight of the alloy, where the alloy does not include copper.

19. Burning-on alloy for the production of ceramically veneered dental restorations, comprising ingredients according to the following table:

| | |
|---|---|
| cobalt | 55-65 percent by weight, |
| chromium | 20-30 percent by weight, |
| tungsten | 4.2-8.2 percent by weight, |
| molybdenum | 3.8-8.5 percent by weight, |
| gallium | 2-4 percent by weight, |
| silicon | 0-2 percent by weight, |
| manganese | 0.05-1.9 percent by weight, |
| nitrogen | 0-0.4 percent by weight, |
| carbon | 0-0.2 percent by weight, |
| vanadium, tantalum, iron, titanium, zirconium, hafnium | in total 0-5 percent by weight, |
| nickel | 0-0.1 percent by weight, |
| platinum group metals, rhenium, gold, silver | in total 0-0.09 percent by weight, |
| other metals, semi-metals and impurities | 0-1 percent by weight, | the percent by weight data are in each case based on the total weight of the alloy, where the alloy does not include niobium and copper.

* * * * *